(12) United States Patent
Farkas et al.

(10) Patent No.: US 11,885,788 B2
(45) Date of Patent: *Jan. 30, 2024

(54) APPARATUS AND METHOD FOR MULTIMODE ANALYTICAL SENSING OF ITEMS SUCH AS FOOD

(71) Applicant: SafetySpect, Inc., Sherman Oaks, CA (US)

(72) Inventors: Daniel L. Farkas, Sherman Oaks, CA (US); Li Kang, Sherman Oaks, CA (US); Stanislov Sokolov, Sherman Oaks, CA (US); Fartash Vasefi, Sherman Oaks, CA (US); Alireza Akhbardeh, Sherman Oaks, CA (US)

(73) Assignee: Safety Spect, Inc, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,568

(22) Filed: Feb. 25, 2022

(65) Prior Publication Data

US 2022/0268751 A1 Aug. 25, 2022

Related U.S. Application Data

(63) Continuation of application No. 16/358,531, filed on Mar. 19, 2019, now Pat. No. 11,280,777.
(Continued)

(51) Int. Cl.
*G01N 33/12* (2006.01)
*G01N 21/49* (2006.01)
(Continued)

(52) U.S. Cl.
CPC ............. *G01N 33/12* (2013.01); *G01N 21/49* (2013.01); *G01N 21/55* (2013.01); *G01N 21/645* (2013.01);
(Continued)

(58) Field of Classification Search
CPC ........ G01N 33/12; G01N 21/49; G01N 21/55; G01N 21/645; G01N 21/65;
(Continued)

(56) References Cited

U.S. PATENT DOCUMENTS 7,808,633 B2 * 10/2010 Maier .................... G01J 3/0294
356/73
8,013,991 B2 * 9/2011 Maier .................... G06V 20/69
356/73
(Continued)

*Primary Examiner* — Tung S Lau

(57) ABSTRACT

A multimode biological sample inspection apparatus and method is provided. The apparatus includes an illumination hardware arrangement comprising transmission and sensing hardware configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample by constructing a multidimensional dataset comprising at least one spatial dimension and at least one spectral dimension from the scan results and analyzing the multidimensional dataset. The processing hardware is configured to employ the attributes of at least one biological sample and alter the protocol.

1 Claim, 11 Drawing Sheets

Related U.S. Application Data

(60) Provisional application No. 62/645,514, filed on Jun. 19, 2019.

(51) Int. Cl.
  *G01N 21/55* (2014.01)
  *G01N 21/65* (2006.01)
  *G01N 21/64* (2006.01)
  *G06N 20/00* (2019.01)

(52) U.S. Cl.
  CPC ....... *G01N 21/65* (2013.01); *G01N 2201/127* (2013.01); *G06N 20/00* (2019.01)

(58) Field of Classification Search
  CPC ............. G01N 2201/127; G01N 21/94; G01N 21/359; G01N 2021/1734; G01N 2021/1738; G01N 2021/3595; G01N 21/3563; G01N 21/4738; G01N 2021/479; G01N 2201/0221; G01N 21/6456; G06N 20/00; G06N 3/045
  See application file for complete search history.

(56) References Cited

U.S. PATENT DOCUMENTS

| | | | |
|---|---|---|---|
| 11,280,777 B2* | 3/2022 | Farkas | G01N 33/12 |
| 2006/0281068 A1* | 12/2006 | Maier | G01N 21/65 |
| | | | 435/6.12 |
| 2007/0153268 A1* | 7/2007 | Panza | G01N 21/65 |
| | | | 356/301 |
| 2012/0035442 A1* | 2/2012 | Barman | G01J 3/0208 |
| | | | 600/316 |
| 2012/0078524 A1* | 3/2012 | Stewart | G16H 50/70 |
| | | | 702/19 |
| 2015/0294076 A1* | 10/2015 | Treado | G16B 40/00 |
| | | | 506/13 |
| 2016/0012591 A1* | 1/2016 | Remiszewski | G01N 21/314 |
| | | | 382/133 |

* cited by examiner

APPARATUS AND METHOD FOR MULTIMODE ANALYTICAL SENSING OF ITEMS SUCH AS FOOD

The present application is a continuation of co-pending U.S. patent application Ser. No. 16/358,531, filed Mar. 19, 2019, inventors Daniel L. Farkas, et al., entitled "Apparatus and Method for Multimode Analytical Sensing of Items Such as Food," which claims priority based on U.S. Provisional Patent Application Ser. No. 62/645,514, filed Mar. 20, 2018, inventors Daniel L. Farkas, et al., entitled "Devices and methods for multi-mode analytical sensing, combinations of fluorescence, reflectance, scattering or Raman analysis of food samples," the entirety of both of which are incorporated herein by reference.

BACKGROUND OF THE INVENTION

Field of the Invention

The present invention relates generally to the field of analyzing items such as food, and more specifically, to the optical inspection of items such as food for multiple issues, including but not limited to composition, quality and identity, spoilage, parasites, disease, adulteration, contamination, and other relevant issues and attributes.

Description of the Related Art

Food composition is of great interest. Assessing the composition of food, quantitatively and reproducibly, is beneficial in avoiding unintended and undesirable scenarios, ranging from a product not being quite what it is stated to be (e.g., a lesser quality fish or olive oil) to intentional adulteration (for financial gain but also including by terrorist intent) to random contamination (such as by bacteria, some of which may be lethal). These issues constitute the application domain of, respectively, food quality, food defense, and food safety. Given the place food occupies in modern society, and the possible extreme implications of any negative events, bringing the best testing to the task of ensuring the quality and safety of the food supply is of great interest.

Unfortunately, some of the currently methods employed in food inspection (molecular/biochemical/biophysical, such as polymerase chain reaction (PCR), chromatography, mass spectrometry, etc.) are too slow to yield usable results in real time, and due to the time required to perform an analysis, tend to rely on random and very sparse sampling.

Optical imaging is an approach rapidly growing in popularity. Recent developments have facilitated the production of smaller, less expensive, more efficient, and faster light sources and detectors. However, when applied to food samples, the accuracy of optical detection techniques can be limited due to factors such as low penetration depth and lack of contrast, especially for low biomarker concentrations.

Recently more portable hand-held systems have been developed with limited capabilities in, for example, food quality, safety, and adulteration applications. Machine Vision/RGB Color imaging is the simplest form of measurement that examines visible range color characteristics with low to moderate specificity and accuracy. Multicolor/hyperspectral imaging can offer compositional analysis beyond standard machine vision. Typically, reflectance hyperspectral imaging captures more extensive and accurate data (and can generate more useful information and spectral signatures) in the expanded wavelength range from UV to Infrared, but still has relatively limited specificity. These single method systems are best suited for more mundane tasks such as sorting color, size, and shape, or simple tasks such as identifying foreign objects such as metal or plastic in food. Infrared imaging can capture more unique chemometric data than the visible range (color), albeit at a higher cost.

It would therefore be beneficial to offer a device or method for inspecting items such as food, but also items such as plants, that avoid the issues associated with previous designs. It would be particularly beneficial to offer a device or method that can be used to quickly and efficiently assess and classify issues with items such as food, including issues such as composition, quality and identity, spoilage, parasites, disease, adulteration, contamination, as well as other issues and attributes.

SUMMARY OF THE INVENTION

According to one embodiment, there is provided a biological sample inspection apparatus, comprising an illumination hardware arrangement comprising transmission and sensing hardware, the illumination hardware arrangement configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample. The processing hardware is configured to employ the attributes of at least one biological sample to alter the protocol.

According to a further embodiment of the present design, there is provided a method for inspecting at least one biological sample, comprising determining a plurality of inspection modes for inspecting the at least one biological sample using a multimode inspection apparatus, determining an inspection protocol for inspecting the at least one biological sample, wherein the inspection protocol comprises inspection settings for the plurality of inspection modes, inspecting at least one biological sample using the multimode inspection apparatus according to the protocol, and altering the protocol based on inspection results for multiple biological samples.

According to another embodiment of the present design, there is provided a biological sample inspection apparatus configured to inspect a biological sample for issues, comprising illumination hardware comprising transmission and sensing hardware configured to illuminate and sense attributes of the biological sample, the illumination hardware configured to inspect the biological sample using multiple inspection configurations from at least one of a fluorescence imaging mode, a reflectance imaging mode, a scattering imaging mode, and a Raman imaging mode, and processing hardware configured to operate the illumination hardware according to a protocol comprising inspection settings for the multiple inspection configurations, wherein the processing hardware receives scan results from the illumination hardware and identifies attributes of the biological sample. The processing hardware is configured to employ the attributes of at least one biological sample and alter the protocol based on the attributes of the one biological sample.

According to a further embodiment of the present design, there is provided a biological sample inspection apparatus, comprising an illumination hardware arrangement comprising transmission and sensing hardware configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample by constructing a multidimensional dataset comprising at least one spatial dimension and at least one spectral dimension from the scan results and analyzing the multidimensional dataset. The processing hardware is configured to employ the attributes of at least one biological sample and alter the protocol.

These and other advantages of the present invention will become apparent to those skilled in the art from the following detailed description of the invention and the accompanying drawings.

BRIEF DESCRIPTION OF THE DRAWINGS

For a more complete understanding of the present disclosure, reference is now made to the following figures, wherein like reference numbers refer to similar items throughout the figures.

DETAILED DESCRIPTION

Figure 1:
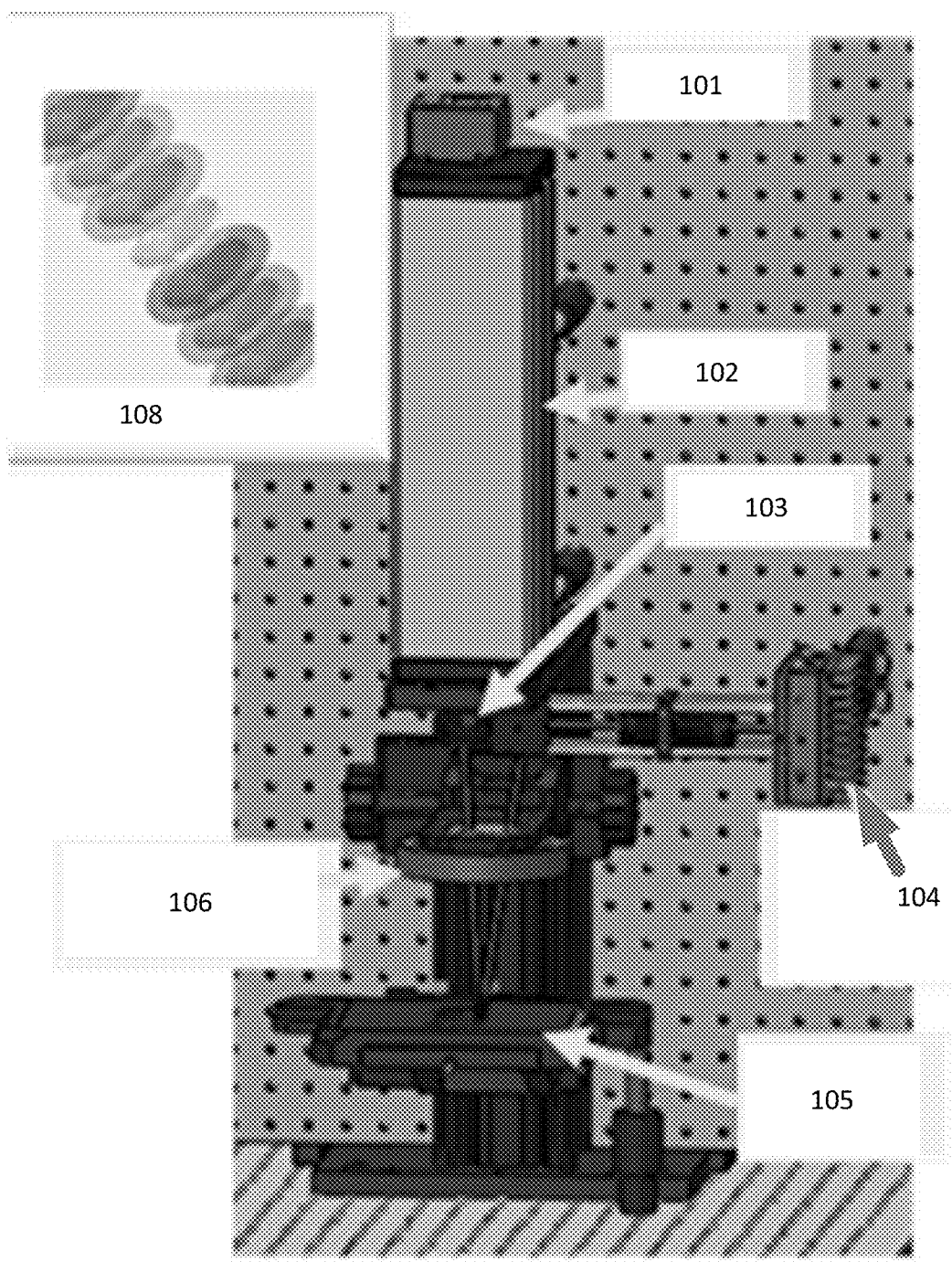
FIG. 1 illustrates one embodiment of the present design including illumination hardware for use with multiple modes of inspection.

The following description and the drawings illustrate specific embodiments sufficiently to enable those skilled in the art to practice the system and method described. Other embodiments may incorporate structural, logical, process and other changes. Examples merely typify possible variations. Individual elements and functions are generally optional unless explicitly required, and the sequence of operations may vary. Portions and features of some embodiments may be included in, or substituted for, those of others.

The present design comprises an analytical multimode optical system that provides at least two methods, including but not limited to fluorescence imaging/spectroscopic, reflectance imaging/spectroscopic, scattering imaging/spectroscopic, and/or Raman imaging/spectroscopic analysis of a sample using at least one transmission source, such as a light source, and potentially a sensor or collection element.

According to the present design, there is provided an incident light beam, for example, traveling to a sample via a wide field, or point illumination at the same region or periphery of the collection optics. The system then collects the emitted light from the sample and forwards the emitted light to a photodetector and/or camera for analysis and viewing. The sample can also be illuminated with a laser to generate Raman emissions, fluorescence emissions, or a scattering pattern (e.g. speckle), which are then collected through the same or different optical path and provided to a spectrograph or sensor for wavelength identification. The present design employs multiple modes of inspection, and the mode or modes employed depend on the specimen being inspected. Further, the present design employs feedback to cross-validate or verify different modes of operation and may in some instances be used to adjust inspection parameters.

The design in one instance includes an inspection tool and an associated method of inspection. Specifically, the design may take the form of a hand-held or possibly small tabletop design, that incorporates multiple transmission and/or sensing devices, such as light emitting and sensing devices, multiple corresponding spectral detection systems, and communication and analysis devices and methods. Such a tool enhances the ability of an on-site inspector to analyze and communicate the compositional, molecular, and chemical constituents of a targeted object/specimen or in a targeted area.

In another aspect, the present design includes an inspection tool and an associated method of inspection. Specifically, the design may include a specialized tabletop, desktop, or hand-held tool that incorporates multiple lighting devices, multiple corresponding spectral detection systems, and a communication and analysis methods. The tool enhances the ability of an on-site inspector to analyze and communicate the compositional, molecular, and chemical constituents of a targeted object or in a targeted area.

As noted, optical imaging is rapidly growing in popularity due to technological advances that have enabled the production of smaller, less expensive, more efficient, and faster light sources and detectors. These new technologies have facilitated the acquisition of more accurate optical image sets, yielding molecular, structural and physiological information from targeted samples. There are many different optical measurement techniques used by industry and academic researchers alike, with each technology usually focusing on a specific property of light (intensity, polarization, wavelength, coherence, temporal change, etc.). However, no single method can rapidly and efficiently provide a comprehensive analysis of items such as food.

As used herein, the term "food" may be employed, and many of the discussions and examples provided relate to fish. However, the design is not so limited, and may be employed with virtually any biological sample or item, including but not limited to animals and plants, with animals including all types of animals, including but not limited to mammals, birds, fish, amphibians, and reptiles, and plants including any type of plant, including but not limited to vegetables, fruits, legumes, flowers, tubers, roots, trees, as well as seeds, nuts, and the like. The design is not limited to the various samples listed herein, nor limited to food per se, but may be employed advantageously with virtually any type of biological material may be inspected using the current teachings.

When inspecting food samples, prior designs have been limited due to factors such as low penetration depth and lack of contrast, especially for low biomarker concentrations.

The present design employs a strategic combination of multiple optical detection technologies in an optical system that becomes multimode, improving chemical and/or biological detection accuracy. Each individual detection method can provide a specific and complementary (sometimes synergistic) piece of information regarding the sample being examined. Thus, by combining a number of these methods, the impact of the individual limitations is minimized, and the combined strengths of the multiple mode results can deliver highly specific results.

The advantages of multimode optical imaging include greatly reducing the time required for the initial detection and enumeration of contaminants, with minimal sample preparation, nondestructive evaluation, fast acquisition times, and visualization of the spatial distribution of numerous components simultaneously. These advantages are highly useful in detecting contaminants in food and assessing safety and quality.

The multiple modes may include but are not limited to the various modes presented and discussed below.

Hyperspectral Imaging (HSI) functions by integrating conventional imaging and spectroscopy to gain spatial and spectral information from an object. HSI is capable of capturing reflectance, transmittance, and fluorescence images in the visible and infrared regions with sub-millimeter spatial resolution and high spectral resolution (10 nm). While HSI was originally developed for remote sensing, it has gained popularity in the field of food safety and analysis with new applications reported in fruits and vegetables, poultry, and meat. Advantages HSI provides in comparison to other techniques (such as RGB imaging, NIR spectroscopy, and multicolor imaging) include the ability to produce spatial and spectral information, multi-constituent information, and sensitivity to minor components.

HSI in the near infrared (NIR) can provide chemical composition about meat, such as prediction of fat, protein, and water content of lamb meat. Moreover, HSI enables the detection of certain bacteria in food, such as *E. coli*.

Fungal growth on food products is of particular concern due to the potential for detrimental effects on population health ranging from allergic reactions and respiratory problems to the production of mycotoxins. HSI has been deployed to identify fungal species such as *Aspergillus flavus, Aspergillus parasiticus, Aspergillus niger* and *Fusarium* spp. which can produce mycotoxins, which are secondary metabolites that are toxic for humans and animals.

A common source of contamination for fresh produce and other raw materials used to produce food is fecal contamination. Multispectral detection of fecal contamination on apples using HSI imaging has been demonstrated. A HSI system with a range of 450 to 851 nm has been used to examine reflectance images of experimentally contaminated apples. Fecal contamination sites may be evaluated using principal component analysis (PCA) with the goal of identifying two to four wavelengths that can be used in an online multispectral imaging system. Actual testing has shown that contamination can be identified using either of three wavelengths in the green, red, and NIR regions.

With the use of HSI in the spectral range of 400-1000 nm, *E. coli* loads in grass carp fish have been measured to evaluate microbial spoilage. Researchers have demonstrated that reflectance HSI in combination with multivariate analysis had the ability to rapidly and non-invasively quantify and visualize the *E. coli* loads in grass carp fish flesh during the spoilage process. Distribution maps of samples examined using HSI may be found in Cheng, J. H., and Sun, D. W., "Rapid quantification analysis and visualization of *Escherichia coli* loads in grass carp fish flesh by hyperspectral imaging method," *Food and Bioprocess Technology*, 8(5), 951-959 (2015), the entirety of which is incorporated herein by reference, illustrating *E. coli* contamination. Such distribution maps provided detailed information of postmortem spoilage development in grass carp flesh.

One of the main advantages that HSI has over conventional spectroscopy methods is its ability to provide visual distribution maps of contamination in a pixel-wise manner. Multiplication of regression coefficients of a multiple linear regression model by the spectrum of each pixel in the image provides a prediction map showing the distribution of *E. coli* within the fish flesh. In the Cheng and Sun reference, different *E. coli* loads are graphically represented by colors from blue, (representing low or no bacteria growth) to red (representing high bacteria growth).

HSI is a non-destructive tool for direct, quantitative determination of Enterobacteriaceae loads on chicken fillets. Such a process employs partial least squares regression (PLSR) models and root mean squared errors. Such use of HSI entails a simplified PLSR model that predicts Enterobacteriaceae loads in every pixel of the image acquired from HSI, resulting in a new image called a 'prediction map.' The prediction map uses a color scale to represent describe the different microbial loads in each spot of the sample.

Feng, Y. Z., ElMasry, G., Sun, D. W., Scannell, A. G., Walsh, D., and Morcy, N., "Near-infrared hyperspectral imaging and partial least squares regression for rapid and reagentless determination of Enterobacteriaceae on chicken fillets," *Food Chemistry*, 138(2), 1829-1836 (2013) shows an image of a median-filled prediction map using a simplified PLSR model built on wavelengths of 930, 1121, and 1345 nm. The entirety of the Feng et al. reference is incorporated herein by reference. The values under each sample represent predicted Enterobacteriaceae counts in $\log_{10}$ CFU $g^{-1}$. As shown in the Feng et al. representations, when the microbial loads increase, the images shift from a blue color to a more reddish one, reflecting the growth of bacteria on the chicken fillets.

Changes in temperature during cold storage of meat products can also lead to undesirable microbial growths, which may affect food safety. HSI has been used to measure biochemical changes within fresh beef. HSI has shown potential for real-time and non-destructive detection of bacterial spoilage in beef.

HSI in the near-infrared range (900-1700 nm) has been used to determine the total viable count and psychotropic plate count in chilled pork during storage. In one instance, researchers captured NIR hyperspectral images in the reflectance mode every 48 hours from each sample. The researchers assumed that meat spoilage would be evident at a microbial load of 107 CFU per gram or $cm^2$ and established a cut-off point of 106 CFU/g as an acceptable threshold of freshness. Differences were observed in the wavelength range between 1300 and 1600 nm, where fresh samples had lower absorbance than spoiled samples, where results are shown in Barbin, D. F., ElMasry, G., Sun, D. W., Allen, P., & Morsy, N., "Non-destructive assessment of microbial contamination in porcine meat using NIR hyperspectral imaging," *Innovative Food Science & Emerging Technologies*, 17, 180-191 (2013), the entirety of which is incorporated herein by reference. This spectral region (wavelength range between 1300 and 1600 nm, is commonly assigned to N—H stretch of proteins (amines and amides) and their interactions with water. This spectral region suggests the occurrence of proteolytic changes, the main indicator for the onset of spoilage in meat products.

Another use of HSI is fluorescence HSI coupled with multivariate image analysis techniques utilized for the detection of fecal contaminates on spinach leaves. Violet fluorescence excitation may be provided at, for example, 405 nm with light emission was recorded from 464 to 800 nm. Partial least square discriminant analysis (PLSDA) and wavelength ratio methods may be compared for detection accuracy for fecal contamination. In one study, the PLSDA model had 19% false positives for non-fresh post storage leaves. A wavelength ratio technique using four wavebands (680, 688, 703 and 723 nm) has been used to identify 100% of fecal contaminates on both fresh and non-fresh leaves.

Detection of fecal contamination on cantaloupes using HS fluorescence imagery has been employed. HS images of cantaloupes artificially contaminated with a range of diluted bovine feces have in one instance been acquired from 425 to 774 nm in response to ultraviolet-A (320 to 400 nm) excitation. Evaluation of images at emission peak wavelengths indicate that 675 nm exhibits a greatest contrast level between contaminated and untreated surface areas. Two-band ratios compared with the single-band images enhanced the contrast between the fecal contaminated spots and untreated cantaloupe surfaces.

Methods may also be employed to classify fecal contamination on leafy greens. Such methods may, for example, utilize HS fluorescence imaging system with ultraviolet-A excitation (320-400 nm) to provide detection of bovine fecal contaminants on the abaxial and adaxial surfaces of romaine lettuce and baby spinach leaves. For both lettuce and spinach, the detection of fecal matter may best be obtained using the ratio of the signal from 666 nm divided by that from 680 nm, with values of 0.98 for romaine lettuce and 0.96 for baby spinach representing a level indicating contamination.

Another technique that may be employed in the current design is Raman Spectroscopy and Spectral Imaging. Raman spectroscopy is a non-destructive spectroscopic technique, based on the vibrational properties of the constituent molecules, that provides molecular information about the sample under examination. The Raman signal results from molecules excited by a small amount of incident light at a specific wavelength. The remitted light has some photons shifted to different wavelengths by the addition or subtraction of vibrational energy from some of the tissue intra-molecular bonds. Contrast is achieved when the tissue molecular constituents differ such that the Raman signals from two tissues have different wavelength distributions. Raman Spectral Imaging (RSI) intertwines Raman spectroscopy and digital imaging to visualize the composition and structure of a target, which is useful in food safety and analysis. Historically, Raman imaging systems have only been able to perform Raman measurement at a microscopic level. Such systems were unable to evaluate whole surfaces of individual foods. Recent studies have shown a benchtop point-scanning Raman chemical imaging system designed and developed for food safety research. Although its signal-to-noise is low, Raman imaging is a highly specific and sensitive technique that allows for the detection of particular chemicals at low concentrations, such as melamine particles in dry milk.

One study aimed at the detection and differentiation of important food and waterborne bacteria (*E. coli, Staphylococcus epidermidis, Listeria monocytogenes*, and *Enterococcus faecalis*) used surface-enhanced Raman spectroscopy (SERS) coupled with intracellular nanosilver as SERS substrates. Variations observed in the spectral patterns of bacterial pathogens resulted from different quantity and distribution of cellular components such as proteins, phospholipids, nucleic acids, and carbohydrates. SERS coupled with statistical analysis is useful in discriminating and detecting bacterial cells, spores, and viruses.

A portable Raman sensor system has been presented with an integrated 671 nm microsystem diode laser as excitation light source for the rapid in situ detection of meat spoilage and bacteria. The system used in this situation demonstrates a reduction in form factor enabled by recent advances, where such a system includes three main components: a handheld measurement head with a laser driver electronics board, the Raman optical bench, and a battery pack. Such a system has been employed to rapidly detect meat spoilage in specific pork cuts, musculus longissimus dorsi (LD) and musculus semimembranosus (SM). The total number of mesophilic aerobic microorganisms on the surface of the meat exhibit possible correlations of bacterial growth with the measured Raman spectra. Concentrations of melamine have been successfully measured in this manner in wheat gluten, chicken feed, and processed foods such as cake and noodles.

Another technique potentially employed in the present design is Speckle (scattering) Imaging. Undesirable microorganisms capable of causing spoilage and poisoning include bacteria, yeast, and mold. Laser speckle imaging has been introduced in this field of application to monitor moving particles in optically inhomogeneous media by analyzing time-varying laser speckle patterns in assessing meat quality and detecting contaminants. Unlike multiple light scattering in meat, which exhibits static and deterministic speckle intensity patterns, light paths associated with the movements of living microorganisms result in time-varying changes in speckle intensity patterns. By detecting the decorrelation in the laser speckle intensity patterns from tissues, the living activities of microorganisms can be detected.

Another advantage of speckle imaging is the ability to examine meats sealed with transparent packaging, as this method detects time-varying signals in reflected laser beams without loss of fidelity due to transparent plastic. Bacterial colonies can be detected within a few seconds using speckle imaging. The method provides an efficient and effective way to detect live bacteria in food products. Speckle imaging systems sense the presence of bacterial colonies and other contaminants in both food and water One study detected and quantified various levels of contamination using chicken breast meat samples. Meats contaminated with bacteria had significant decreases in auto-correlation values over time, whereas the control group (meat treated with a PBS solution) did not show any major changes. The meat treated with a high concentration of bacteria had more significant changes over time compared with the meat treated with a low concentration of bacteria. Moreover, the decrease in the autocorrelation value was proportional to the concentration of the treated bacteria. The measured autocorrelation values were all statistically different from one another ($p<0.001$) and decreases in autocorrelation were proportional to the concentration of bacteria. Thus spontaneous bacterial activity caused strong decorrelation in laser speckle dynamics.

Yoon J, Lee K, Park Y., "A simple and rapid method for detecting living microorganisms in food using laser speckle decorrelation," arXiv preprint arXiv:1603.07343, 2016 Mar. 18. illustrates assessing bacterial activity in meat. The Yoon et al. reference, the entirety of which is incorporated herein by reference, shows representative autocorrelation amps in meat treated with various concentrations of bacteria at various time lags, including averaged C(tau) values as a function of the time lag, as well as quantification of the autocorrelation values at tau equal to 10 seconds.

One label-free bacterial colony phenotyping technology is the BARDOT (Bacterial Rapid Detection using Optical Scattering Technology) system, which can provide classification for several different types of bacteria. A certain speckle formation allows for the detection and identification of these bacterial species. As the center diameter of the *Bacillus* spp. colony grows from 500 to 900 microns, the average speckle area decreases two-fold in certain experiments and the number of small speckles increases sevenfold. As *Bacillus* colonies grow, the average speckle size in the scatter pattern decreases and the number of smaller speckle increases due to the swarming growth characteristics of bacteria within the colony. Real-time detection and identification of *Salmonella* colonies grown from inoculated peanut butter, chicken breast, and spinach or from naturally contaminated meat using BARDOT technology (90 to 100% accuracy) in the presence of background microbiota from naturally contaminated meat.

The present design may be applied in various areas, including but not limited to the following. In the field of seafood safety, *Salmonella enterica* and *Escherichia coli* are members of the Enterobacteriaceae family and are widely found in the environment. They typically spread to humans through the fecal-oral route or contact with contaminated water sources. While most strains of *E. coli* are harmless, there are several pathogenic variants that cause gastrointestinal illness and can lead to health complications. Pathogenic *E. coli* are associated with foods such as animal products and fresh produce. Because *E. coli* are abundant in human and animal feces, tests for generic *E. coli* levels in food are often used to indicate recent fecal contamination or unsanitary processing. These tests have been performed using culture-based methods that require 24-48 hours using rapid techniques or 5-7 days with traditional means.

*S. enterica* is the leading bacterial cause of foodborne illness in the United States and is associated with a variety of foods, including poultry, fresh produce, dairy products, and some low-moisture foods. Detection of *S. enterica* in foods using traditional culture methods is laborious and time-consuming, requiring 4-5 days for confirmation of a positive sample. Rapid detection methods, such as real-time polymerase chain reaction (PCR), have been developed for *S. enterica*. These methods can typically be completed within about 1-3 hours. However, they generally require at least a primary enrichment step and sometimes a selective enrichment step, which can add up to 24-48 hours to the procedure.

The use of multimode hyperspectral imaging (HSI) as a rapid screening technique reduces the time required for the initial detection and enumeration of contamination on foods. Hyperspectral imaging integrates spectroscopic and imaging techniques to enable direct identification of different components and their spatial distribution in the tested sample. The resulting three-dimensional dataset or 'hypercube' contains two spatial dimensions and one spectral dimension. The advantages of hyperspectral imaging over traditional methods include no/minimal sample preparation, nondestructive nature, fast acquisition times, and visualization of the spatial distribution of numerous components simultaneously. Previous studies have utilized hyperspectral imaging to determine quality and microbial characteristics of food products and contact surfaces.

HSI combined with chemometrics is employable to detect and enumerate *E. coli* on fresh spinach. Near-infrared HSI can be used to enumerate Enterobacteriaceae on chicken fillets and in certain instances can detect bacterial loads at levels of 2.4-5.2 log CFU/g. Hyperspectral fluorescence imaging has also been used to detect biofilms of *S. enterica* and *E. coli* O157:H7 on food contact surfaces.

Fluorescence spectroscopy has been used previously to identify and differentiate foodborne bacteria. Fluorescence spectroscopy is a simple, non-destructive, non-invasive and relatively inexpensive analytical method. In comparison with other classical analytical methods, fluorescence spectroscopy provides enhanced selectivity, high sensitivity to a wide array of potential analytes, and has no requirement for consumable reagents or extensive sample pre-treatment. This technique is based on the intrinsic fluorescence of bacterial cell components. When examined with ultraviolet light, aromatic amino acid residues (tryptophan, tyrosine, phenylalanine), nucleic acids, and co-enzymes are intrinsic fluorophores. However, due to the multicomponent nature of items such as foods, their fluorescence spectra are complex and chemometric methods using multivariate analysis are needed to extract contaminant specific information. The present design may vary both the excitation and detection wavelengths, and measure both reflectance and fluorescence emission properties of a food sample. The system is adjusted or may adjust for specific foods and contaminants. For biological tissues, dual or multiple excitation fluorescence can increase the specificity and accuracy of classification and quantification of specific sources of fluorescence. When the system employs dual excitation wavelengths, fluorescence emission contributions of food contaminants can be more precisely detected, and the system may disregard other irrelevant or unnecessary fluorescence components of the food sample. Ratiometric versions of this approach may be employed.

Laser Speckle Contrast Imaging (LSCI) is a wide field of view, non-scanning optical technique used in observing, for example, blood flow in medical applications or live bacteria colonies in food samples. Speckles are produced when coherent light scattered back from biological tissue is diffracted through the limiting aperture of focusing optics. Mobile scatterers, i.e. scattering objects or items that are moving, cause the speckle pattern to blur. The present design may employ a model that inversely relates the degree of blur, called "speckle contrast," to the scatterer speed. In tissue, red blood cells are the main source of moving scatterers. Bacteria movement acts as a virtual contrast agent.

In the case of seafood adulteration, for example, the present system is a multimode hyperspectral image acquisition system for real-time assessment of fish quality and adulteration. With increased seafood imports and limited monitoring, fraud and deception in seafood marketing is a growing food safety concern. A desired high quality fish may be substituted with a lower quality, less costly fish unbeknownst to the purchaser and/or consumer. The flesh of many fish species is similar in taste and texture and, therefore, identifying species in fillet form can be challenging, especially after preparation for consumption. One survey by the National Marine Fisheries Service's National Seafood Inspection Laboratory (NSIL) found that over a nine-year period, 37% of fish and 13% of other seafood (e.g., shellfish, edible seaweed) from randomly selected vendors were mislabeled.

The present design overcomes the limitations of previous spectroscopic solutions focused on fish quality and authentication through a number of improvements, the main one being the use of a multimode imaging approach that combines multiple imaging methods. One combination is reflectance and fluorescence hyperspectral imaging. Hyperspectral imaging detects various types of fish with high accuracy (i.e. wild versus farmed salmon). The present design identifies and validates key wavelength bands that are central to fish quality assessment and authentication.

In the area of meat adulteration, many individuals worldwide follow a diet that restricts them to eating only halal food products. Dietary restrictions such as halal, have several guidelines to follow. Islamic Law does not allow Muslims to eat or use any product derived from pig. Moreover, halal consumers have become concerned about issues such as pork substitution, undeclared blood plasma, use of prohibited ingredients, and non-halal methods of slaughter, among other concerns. One of the main authenticity issues which is common among Muslim consumers is the need to determine whether meat products from halal species have been mixed with similar material from a cheaper non-halal species. Food manufacturers sometimes choose to substitute pork derivatives in food products as they tend to be cheaper and readily available. Such pork derivatives may include pork tissues (e.g. collagen and offal), porcine mechanically recovered meats (MRM) and pork fat (lard). Animal fat from one species is often fraudulently used to substitute animal fat from another species. If the substitution contains pork fat, then that product becomes 'haram,' or forbidden by Islamic law. Another form of substitution of meat products is the use of mechanically recovered meat (MRM). MRM describes the residual material off bones that is obtained by machines operating on hydraulic or other pressure principles in such a way that the structure of the material is broken down enough for it to flow in a paste-like form from the bone. Chicken and pork carcasses are the most commonly used material for MRM production today. If pork carcasses are used, the resultant product would be considered haram and not for consumption by Muslim consumers.

The food industry uses porcine blood and its derivatives, plasma and red cells, as food ingredients. Any product where blood is added is unacceptable for Muslim consumers. The need exists for techniques that can determine the authenticity of halal food products.

Several analytical methods that have been developed to detect adulteration rely on protein or DNA analysis. Some protein analysis methods include ELISA, chromatography, and FTIR spectroscopy. Analysis of DNA is typically done through polymerase chain reaction (PCR). ELISA based techniques using polyclonal antibodies have several disadvantages including limited production, variable affinity, and the requirement for extensive purification procedures to eliminate cross-reactivity for a particular species identification. Methods such as PCR can typically be completed within 1-3 hours. However, they generally require at least a primary enrichment step and sometimes a selective enrichment step, which can add up to 24-48 hours to the procedure. Moreover, DNA extraction from food products has several problems and limitations. Food products are made up of carbohydrates, fat, and chemicals that are often inhibitory to the PCR reaction, leading to false results (negative or positive). Furthermore, the standardization of the PCR procedure (sampling to result interpretation) is difficult and requires specific skills and cautious handling to complete. Also, conventional PCR has the limitation of not providing information on the quantitative analysis of the food product. Thus, many of these techniques require long waiting periods to obtain results and therefore are not suitable for rapid assessment of food authenticity.

Multimode hyperspectral imaging (HSI) as a rapid screening technique greatly reduces the time required for detection of prohibited ingredients in halal foods. Hyperspectral imaging integrates spectroscopic and imaging techniques to enable direct identification of different components and their spatial distribution in the tested sample. The resulting three-dimensional dataset or 'hypercube' contains two spatial dimensions and one spectral dimension. The advantages of hyperspectral imaging over traditional methods include no, or minimal, sample preparation, no contact, nondestructive nature, fast acquisition times, and visualization of the spatial distribution of numerous components simultaneously.

The design presented, using multimode imaging, circumvents limitations of other analytical methods. Again, the current design combines several optical imaging methods, for example a combination of reflectance and fluorescence spectroscopy together with dynamic speckle imaging. Fluorescence spectroscopy is a simple, non-destructive, non-invasive and relatively inexpensive analytical method that provides enhanced selectivity, high sensitivity to a wide array of potential analytes, as well as no requirement for consumable reagents or extensive sample pre-treatment. Fluorescence spectroscopy is based on the intrinsic fluorescence of bacterial cell components. When examined with ultraviolet light, aromatic amino acid residues, nucleic acids, and co-enzymes are intrinsic fluorophores. However, due to the multicomponent nature of foods, their fluorescence spectra are complex, and chemometric methods using multivariate analysis are employed to extract contaminant specific information. By varying both the excitation and detection wavelengths and measuring both reflectance and fluorescence emission properties of a food sample, the system can be employed to accurately assess specific foods and contaminants. For biological tissues, dual or multiple excitation fluorescence can increase the specificity and accuracy of classification and quantification of specific sources of fluorescence. The present system employing dual excitation wavelengths allows for more specific detection of fluorescence emission contributions of food contaminants and disregard other fluorescence components of the food sample.

Prior concepts, designs, and studies have utilized a single optical technique to successfully determine authenticity, for example. Multimode optical imaging in accordance with the current design provides greater accuracy in less time. Infrared spectroscopy, for example, is a fast, sensitive, and non-destructive technique that may be used to analyze food products for authenticity studies. Analyzing a food sample using the mid infrared spectrum (4000-400 $cm^{-1}$) can give valuable information about the existence of molecular bonds. Such details can help determine the types of molecules present in the food. Pig derivatives (such as lard) in any food product are prohibited by halal food consumers. The current system may employ Fourier Transform Infrared Spectroscopy (FTIR) combined with attenuated total reflectance (ATR) and partial least square regression (PLSR) to detect the presence of lard in food items.

The FTIR spectra of both mutton body fat (MBF) and lard is shown in Jaswir, I., Mirghani, M. F. S., Hassan, T. H., and Said, M. Z. M., "Determination of lard in mixture of body fats of mutton and cow by Fourier transform infrared spectroscopy," *Journal of oleo science,* 52(12), 633-638 (2003), the entirety of which is incorporated herein by reference. One representation in Mirghani, et al. shows distinct differences in the raw spectra obtained between MBF and lard. The frequency region 3010-3000 $cm^{-1}$ indicates a significant difference between lard and MBF. The lard spectrum has a sharp band at higher frequency (3009 $cm^{-1}$) than MBF which has a shoulder peak at low frequency (3001 cm$^{-1}$). FTIR inspection provides a clear and concise manner to identify lard in a mixture of other fats.

Another method employable in the current design is visible and near infrared reflectance spectroscopy (VIS-NIRS), which can be useful to discriminate meat and meat juices from different livestock species. In one trial, meat samples corresponding to beef, llamas, and horses were homogenized and their spectra collected in reflectance (in the range of 400-2500 nm). VIS-NIRS combined with partial least square regression analysis can be an accurate tool to discriminate meat obtained from beef, llama and horse through analysis of the spectral data of minced meat, collected by reflectance.

NIR hyperspectral imaging technology may be employed to, for example, to detect adulteration in meat. Previous testing resulted in the identification of four 'important' wavelengths later used to predict the level of adulteration in minced lamb meat. Spectral data collected from NIR hyperspectral imaging combined with multivariate analysis can be successfully used to detect adulteration in meat.

Raman spectroscopy in combination with chemometrics can be employed for rapid determination of beef adulteration with horsemeat. Raman spectra of meat samples have been gathered at frequencies between 200 and 2000 cm$^{-1}$. Spectral differences and unique bands that belong to horse fat may be observed. These spectral differences between horse and beef are from the unique bands of horse fat at 919, 974, 1215 cm$^{-1}$. The system may employ these unique bands and may examine samples for bands that belong to horse fat in horsemeat and can develop a level of confidence that the sample of beef being examined has been adulterated with horsemeat. Some of the advantages of techniques such as Raman Spectroscopy over other non-optical methods are short analysis time (in 30 seconds) and no requirement for time consuming sample preparation procedures. Boyaci, I. H., Temiz, H. T., Uysal, R. S., Velioğlu, H. M., Yadegari, R. J., and Rishkan, M. M., "A novel method for discrimination of beef and horsemeat using Raman spectroscopy," *Food chemistry*, 148, 37-41 (2014) illustrates an original Raman spectra of horsemeat and beef samples, as well as the first derivative of the Raman spectra.

Several techniques have been proposed for detecting meat adulteration and food fraud, namely, for halal authentication. Each approach provides a rapid and accurate analysis of the sample being examined, enabling the detection of any undesirable. The present approach integrates several optical imaging methods to bring about the highest level of accuracy and efficiency for food authentication. Thus, in present day, multimode optical imaging is the most advanced and well-equipped technique for determination of halal authenticity.

The present design therefore comprises a multimode hyperspectral imaging system. Due to the multicomponent nature of biological items such as foods, their reflectance or fluorescence spectra are complex. Chemometric methods using multivariate analysis are employed by the present system to extract contaminant specific information. By varying both the excitation and detection wavelengths and measuring both reflectance and fluorescence emission properties of a food sample, profiles may be assessed, refined, and employed when examining specific foods and contaminants. For biological tissues, dual or multiple excitation fluorescence can increase the specificity and accuracy of classification and quantification of specific sources of fluorescence. The combination of different spectroscopic methods (such as fluorescence and NIR spectroscopy) circumvents single method inherent limitations and can employ optical sensing for in situ mycotoxin detection. Additional chemometric tools eliminate factors related to disturbing the specimen and enable extraction of desired biochemical information with respect to contamination with fungi and/or mycotoxins.

The multimode hyperspectral imaging system may operate in fluorescence and reflectance modes and may concurrently, or at a different time, employ speckle imaging. One example of such a system is presented in FIG. 7. The system uses spectral band sequential imaging on the detection side. To ensure high signal to noise level, camera and spectral selection filter integration time is optimized for each spectral band from visible to the near infrared. The illumination module uses two independent light sources to provide illumination for fluorescence excitation and reflectance measurements using three computer-controlled LED illumination rings. The UVA (375 nm) and blue/violet (420 nm) LED rings provide fluorescence excitation. White LEDs will be used for reflectance illumination. The HSi-440CO Hyperspectral Imaging System (Gooch & Housego, UK, originally developed by ChromoDynamics, Inc.) incorporated in the proposed system can image and analyze multiple signals in fixed and living cells at video rates. Its tunable filter can switch wavelengths within microseconds. The system acquires multi-wavelength, high-spatial and spectral resolution image datasets, and can compute and display quantitative signal-specific images in near real-time. The spectrally controllable image capture system can record spectral images of food samples in wavelengths ranging from 450 nm through 800 nm. The system is configured as a tabletop platform where illumination and detection operate above the food sample.

In this system, time-varying speckle signals can be quantitatively addressed with speckle correlation time. A sample containing living microorganisms has a correlation time shorter than a static one, and thus contaminated food is less time-correlated compared to fresh food due to the spontaneous motility of microorganisms. Correlation time of scattered light from samples, as well as presence and activity of microorganisms are quantitatively analyzed.

FIG. 1 includes a camera 101 at the top, acousto-optical tunable filter (AOTF) 102, lens 103, ring illumination element 104, laser (speckle imaging) arrangement 105, and sample holder 106 to hold the sample. Shown as representation 108 in the upper left corner are various biological sample scans representing scanning using different modes of the multimode apparatus. Spectral selection can be implemented in illumination optical path and/or detection optical paths. The methods of spectral selection may include a filter wheel, an acousto-optical tunable filter (AOTF), a liquid crystal tunable filter (LCTF), DMD based spectral filter, Fabry Perot based spectral filter, and/or diffraction based spectral filters such as gratings and prisms (not shown in this view). Any or all of the imaging components can be offered in this multimode imaging system.

Regarding processing the images received, consider I (x,y,t) the image of the sample at time t. The correlation coefficient between two images of the sample at different times is given by the normalized autocorrelation function:

$$C(x, y, t) = \frac{1}{T - \tau} \sum_{t=1}^{T-\tau} I(x, y, t) \cdot I(x, y, t + \tau) \delta t \tag{1}$$

where T is the total acquisition time, δt the time difference, and τ the time lag. In the case of food contamination assessment, the sample is considered and the correlation to be close to the unity. Every decorrelation effect is therefore due to the presence of live microorganisms moving across the sample.

For image correlation and calibration, since each spectral band is recorded at different exposure times to ensure optimized signal to noise ratios, the design employs a calibration method to correct for instrument response (e.g. lens and illumination non uniformity) and exposure time variations. Flat field corrected reflectance image (RI) spectra will be calculated as follows:

$$RI(x, y, \lambda) = \frac{RS(x, y, \lambda) - RD(x, y, \lambda)}{RR(x, y, \lambda) - RD(x, y, \lambda)} \quad (2)$$

where RS is the sample image, RD is the dark current image, and RR is the reference image. The present design may employ, for example, White Spectralon® reflectance and fluorescence targets (Labsphere Inc., North Sutton, NH) to acquire the reference image. The same exposure time will be used for each wavelength during RD and RR image acquisition.

Figure 2:
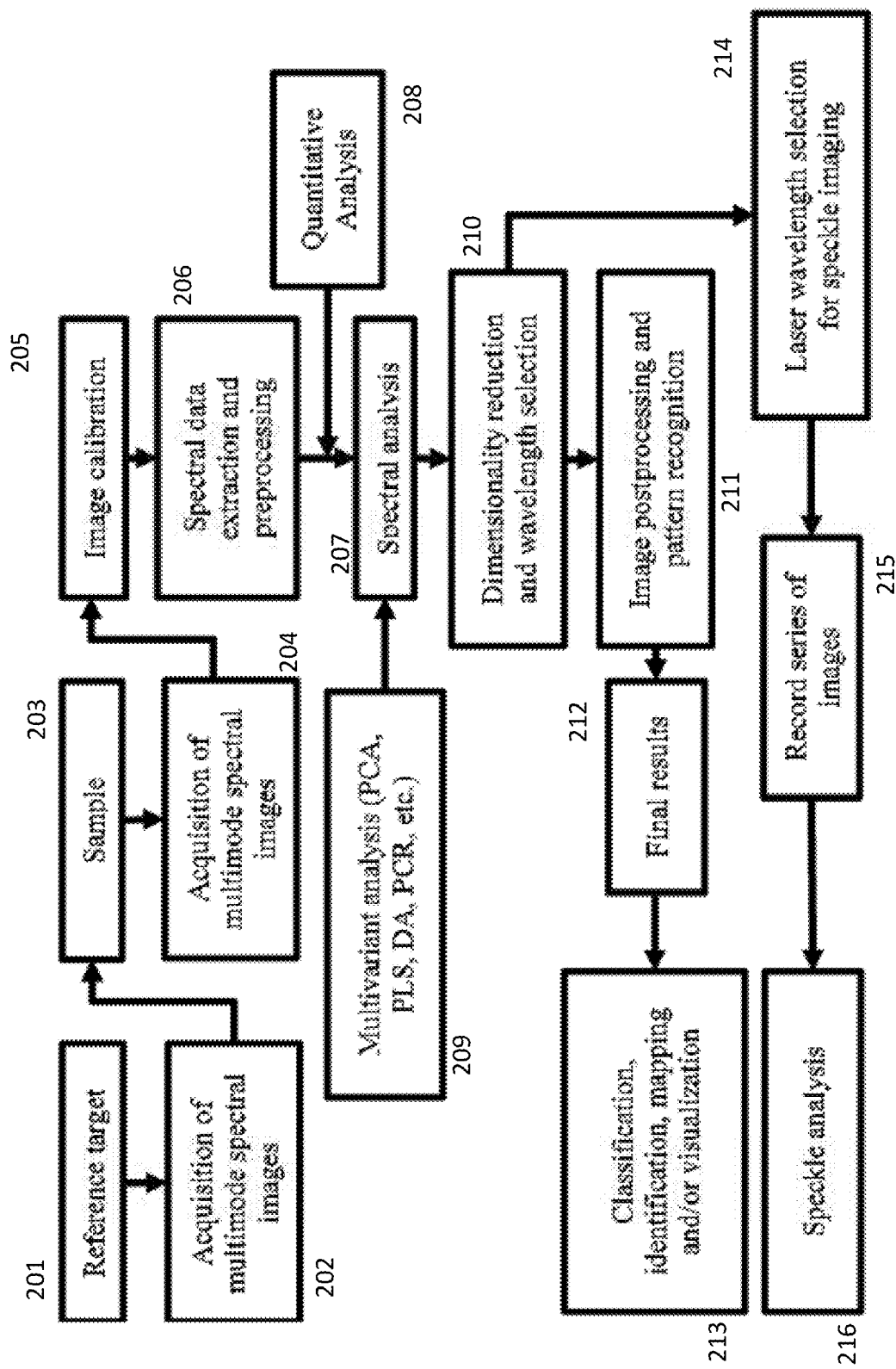
FIG. 2 shows operation in spectral imaging analysis.

For spectral data analysis the system employs an algorithm for data preprocessing to extract fluorescence emission and reflectance spectral data cube, an algorithm for multivariant analysis, and an algorithm for relative quantification of food contaminant concentration in the sample. FIG. 2 shows operation involved in multimode hyperspectral imaging analysis. The system may employ MATLAB software for image analysis. The system selects wavelengths preserving the largest amount of energy among the multimode spectral data with the aid of multivariant analysis, providing maximum discrimination between samples with different contaminant concentrations. Image analysis is typically performed off-line after image acquisition is completed. The system sorts essential wavelengths from whole spectral data using general visual inspection of spectral curves to more advanced objective approaches such as correlation analysis, analysis of spectral differences from average spectrum, stepwise regression, discriminant analysis, and principal component analysis.

With respect to speckle image analysis, time-varying speckle signals can be quantitatively addressed with the speckle correlation time. A sample containing living microorganisms has a correlation time significantly shorter than a static one. As a result, contaminated food is less time correlated compared to fresh food due to the spontaneous motility of microorganisms. The system quantitatively analyzes correlation time of scattered light from samples and the presence and activity of microorganisms.

If I(x,y,t) represents the image of the sample at time t, the correlation coefficient between two images of the sample at different times is given by the following normalized autocorrelation function:

$$C(x, y, t) = \frac{1}{T-\tau}\sum_{t=1}^{T-\tau} I(x, y, t) \cdot I(x, y, t + \tau)\delta t \quad (3)$$

where T is the total acquisition time, $\delta t$ the time difference, and $\tau$ the time lag. In the case of food contamination assessment, the sample is considered static and the correlation is expected to be close to unity. Every decorrelation effect is due to the presence of live microorganisms moving across the sample, indicating an issue.

The system extracts diagnostic information from multimode/hyperspectral datasets, such as by testing multiple (e.g. six) different spectral segmentation algorithms on the same image data for optimal discrimination. Methods range from relatively simple, established ones (square Euclidean distances, principal components analysis) to more specialized ones (Mahalonobis distances, support vector machines, multivariant analysis) and depend on circumstances.

From FIG. 2, the system employs a reference target at point 201, and may calibrate using the reference target. At point 202, the system acquires multimode spectral images of the reference target and may calibrate in this instance. At point 203, the system is provided with the sample, and at point 204, the system acquires multimode spectral images of the sample. The two images may again be calibrated at point 205, while at point 206 the system performs spectral data extraction and preprocessing. Point 207 represents the spectral analysis performed, where point 208 represents quantitative analysis and point 209 is multivariant analysis, including PCA, PLS, DA, PCR, and/or other analysis techniques. Point 210 employs dimensionality reduction and wavelength selection, provides selected data to image postprocessing and data recognition at point 211, and determines final results at point 212. Point 213 is certain further processing, including classification, identification, mapping, and/or visualization to convey results to persons. Point 214 represents laser wavelength selection for speckle imaging, where point 215 records a series of images. Point 216 provides speckle analysis. Speckle imaging may be provided as an alternate to, or in addition to, the image postprocessing and other functions presented at points 211, 212, and 213.

As may be appreciated, multiple modes may be employed in the current design. While FIG. 2 shows spectral analysis and speckle analysis, different modes may be employed, and in certain instances, available modes may be turned off or not used. For example, if the specimen has a profile wherein certain benefits may be obtained using speckle analysis and infrared imaging, other modes offered (speckle analysis, brightfield imaging, and so forth) present in the device and available for use for inspection may not be employed, particularly if their use does not lend to improved results for the sample considered.

Figure 3:
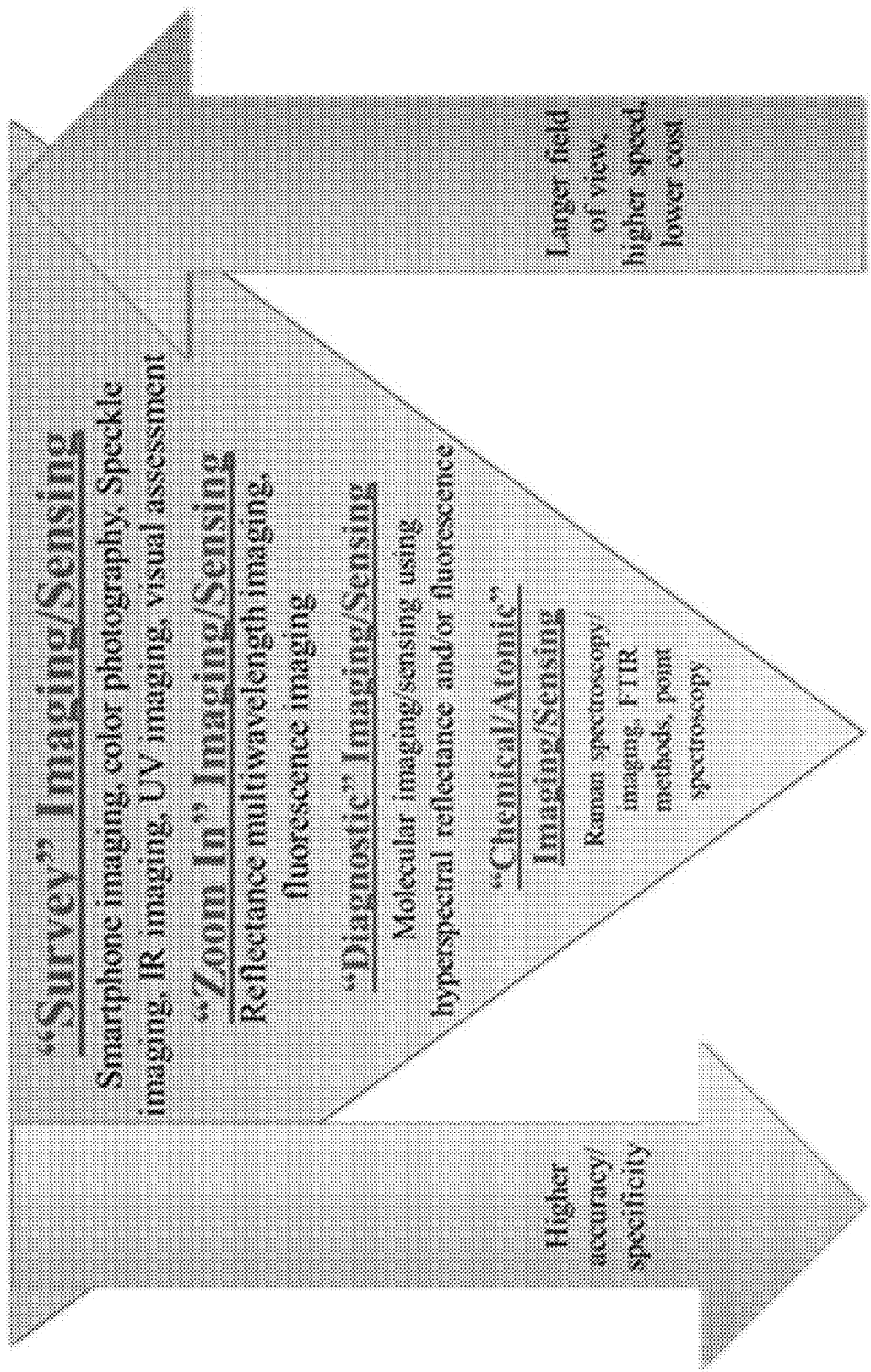
FIG. 3 shows the conceptual methods employable and employed in embodiments of the present design.

FIG. 3 represents using multimode optical imaging to characterize food samples. A series of optical technologies can be used based on the complexity of detection as well as acquisition speed, field of view, type of optical signature to be recorded. The system or a user may select one or more optical methods based on a specific detection problem. In some embodiments, at least two methods in each category shown in FIG. 3 may be used to enhance the accuracy of measurement. From FIG. 3, the least accurate/specific techniques have the largest field of view, have higher speed, and result in a lower cost, while the converse is true for those techniques presented at the bottom of FIG. 3. In descending order, techniques include "Survey" imaging and sensing, such as speckle imaging, UV imaging, etc., followed by "zoom in" imaging and sensing, including for example reflectance multiwavelength imaging, fluorescence imaging, and the like, followed by "diagnostic" imaging and sensing (molecular imaging and sensing using hyperspectral reflectance and/or fluorescence), and "chemical or atomic" imaging and sensing, such as Raman spectroscopy, imaging, FTIR methods, and point spectroscopy.

Figure 4:
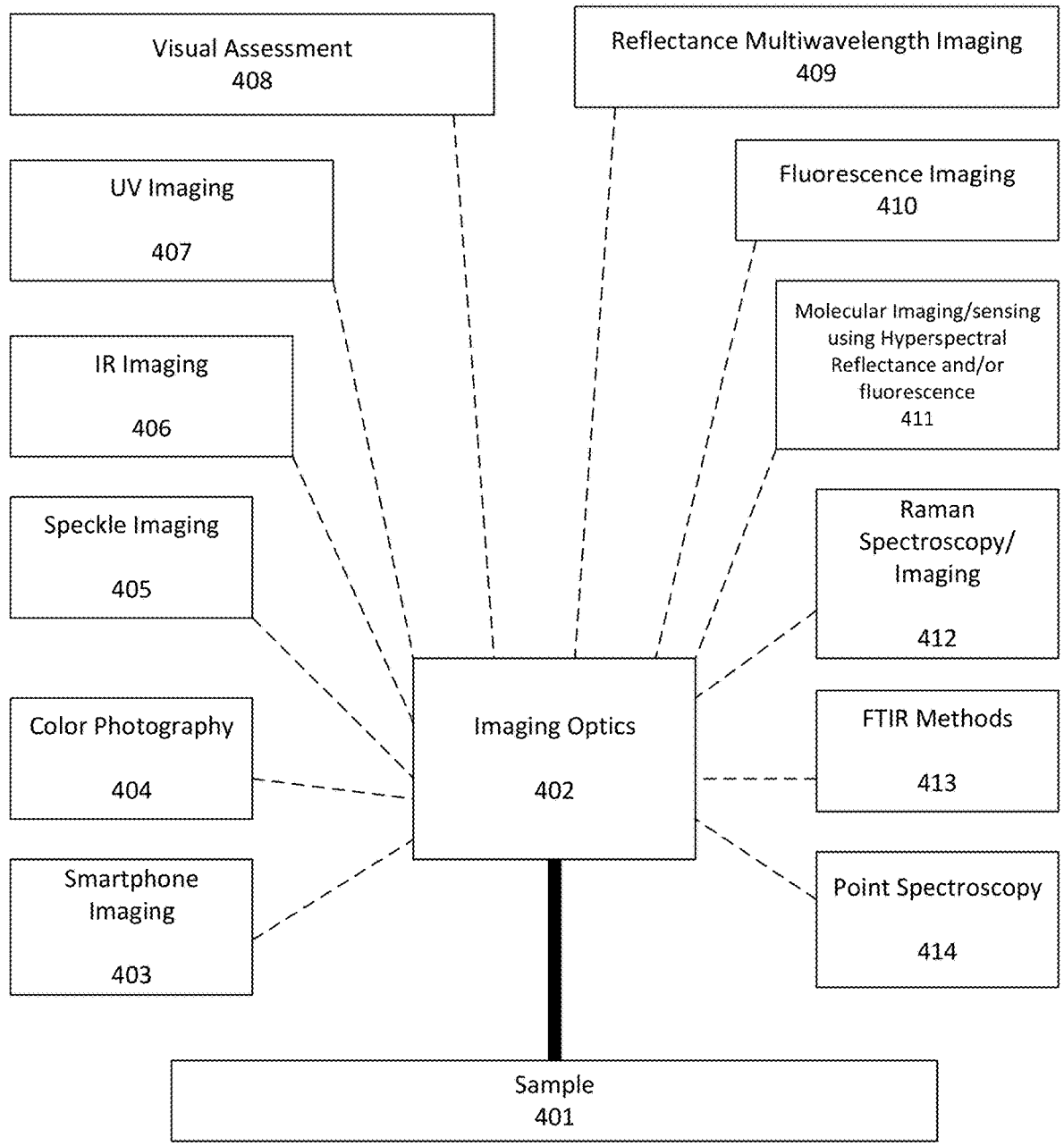
FIG. 4 illustrates a representation of a device used to inspect samples in accordance with the present design.

An alternate version of the design is presented in FIG. 4. From FIG. 4, specimen 401 is shown along with imaging optics 402. Different optics and optical channels or paths may be provided. From there several optional imaging techniques are pictured in accordance with the representative imaging and sensing techniques of FIG. 3. It is to be understood that more techniques may be employed depending on circumstances, and various imaging optics may be employed or in some instances such as simple photography, no optical components besides the named apparatus may be required. Further, the presence of broken lines indicates that all of these components are optional, but in general, more than one technique is employed, with FIG. 1 representing one possible multimode embodiment. From FIG. 4, the system may employ "survey" imaging and sensing components, such as smartphone imaging 403, color photography 404, speckle imaging 405, IR imaging 406, UV imaging 407, and visual assessment 408. "Zoom in" imaging and sensing is represented by reflectance multiwavelength imaging 409 and fluorescence imaging 410, while "diagnostic" imaging and sensing is represented by molecular imaging/sensing using hyperspectral reflectance and/or fluorescence at point 411. "Chemical or atomic" imaging and sensing is represented by Raman spectroscopy/imaging 412, FTIR methods 413, and point spectroscopy 414. Such techniques may be provided concurrently or sequentially.

Figure 5:
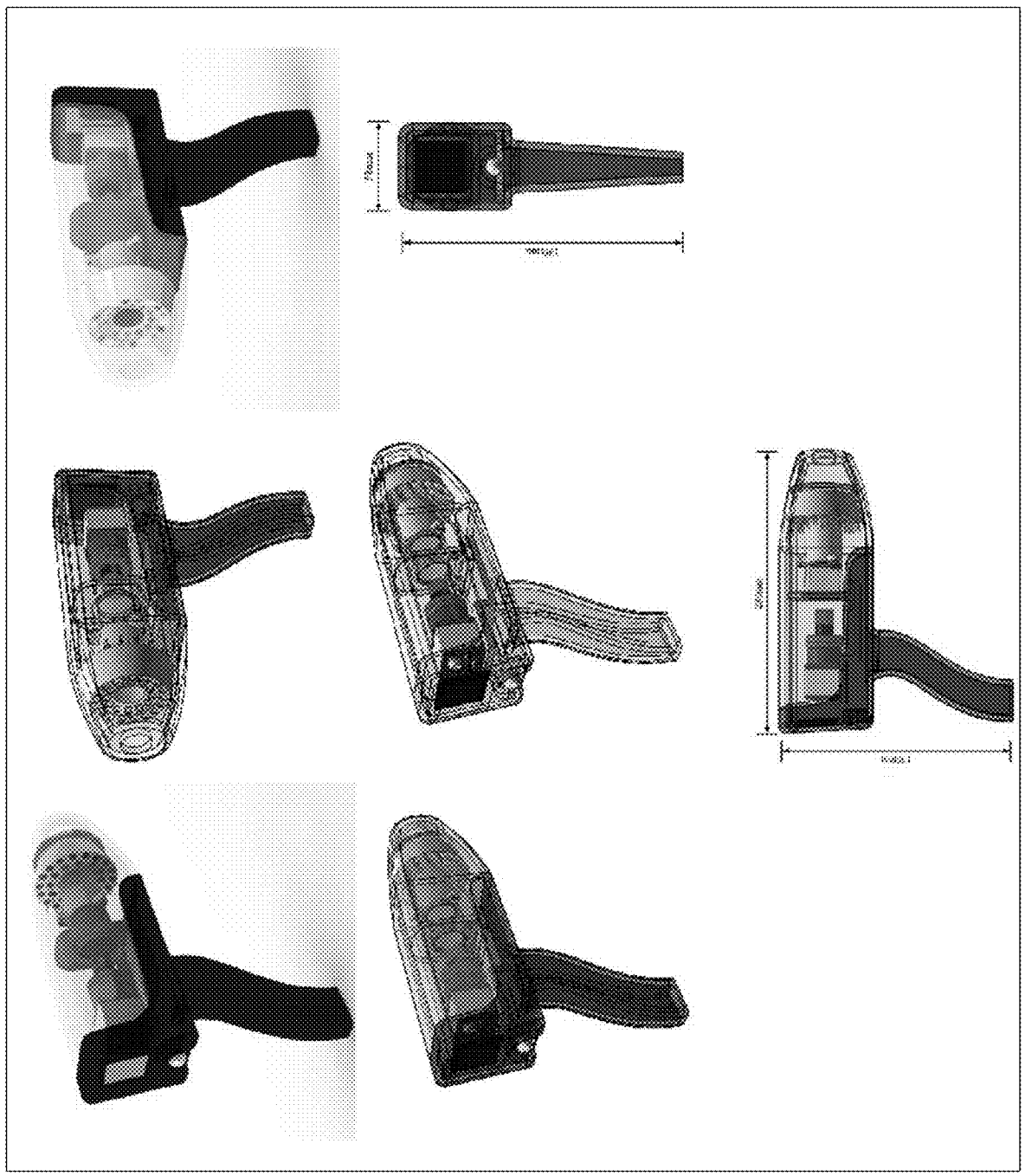
FIG. 5 represents a potential embodiment of a handheld multimode inspection system according to the present design.

The present design may be provided in a tabletop or handheld form, and may take different forms depending on sizing, as well as need for and availability of components. FIG. 5 shows representations of a multimode optical imaging system as a portable platform. The handheld design shown generates illumination for reflectance and or fluorescence using LED ring (polarized or unpolarized) techniques. Reflectance and/or fluorescence emission photons may be filtered by wavelengths or polarization at the detection optical path.

Processing

The system characterizes materials, typically biological materials such as food, drugs, etc. based on multimode spectral analysis. According to the present design, such analysis includes identifying features from different modes of measurement. Feature extraction/selection strategy or methods for different modes of measurement may differ based on measurement physics and biological/chemical characteristics. Examples of feature extraction methods include wavelet transform, statistical features, haralick textural features, fractal analysis, and curvelet transform. The system may employ feature selection methods such as principal component analysis (PCA), independent component analysis (ICA), curvature and/or manifold learning.

Wavelet transform is a mathematical transform to extract information from a signal or an image. In one dimensional wavelet transform, the input signal is represented at different scales called coarse and detail components using a set of basis functions originally from a function called mother function.

The system may, online or offline, include identifying which spectral measurement mode (or combination) will have the highest impact resulting among the top combinations. Optimization is based on a cost function (sensitivity, specificity, area under the curve) from a receiver operating characteristics (ROC) curve. Depending on technology complexity, the system employs desired practical modes.

Based on the practical modes determined, the present design links the biology and chemical components of samples and correlates them with highest differentiating spectral features. Different samples may exhibit differences in this regard, such as fish, beef, plants, fruits, and so forth. The system may run independent measurements using metabolic and/or chemical analysis of samples to validate the biological/chemical differentiation between samples to determine optimal modalities. The system uses these optimal modalities to conduct a pilot study with sample size greater than or equal to a number of samples, such as 100, sufficient for collection and analysis of enough data from a variety of samples in view of other parameters. In the case of fish, for example, the number of samples may include a number of fish species (for example, up to 15 species) and other parameters considered may include attributes such as frozen and thawed versus fresh, farm-raised versus wild-caught, and so forth.

Figure 6:
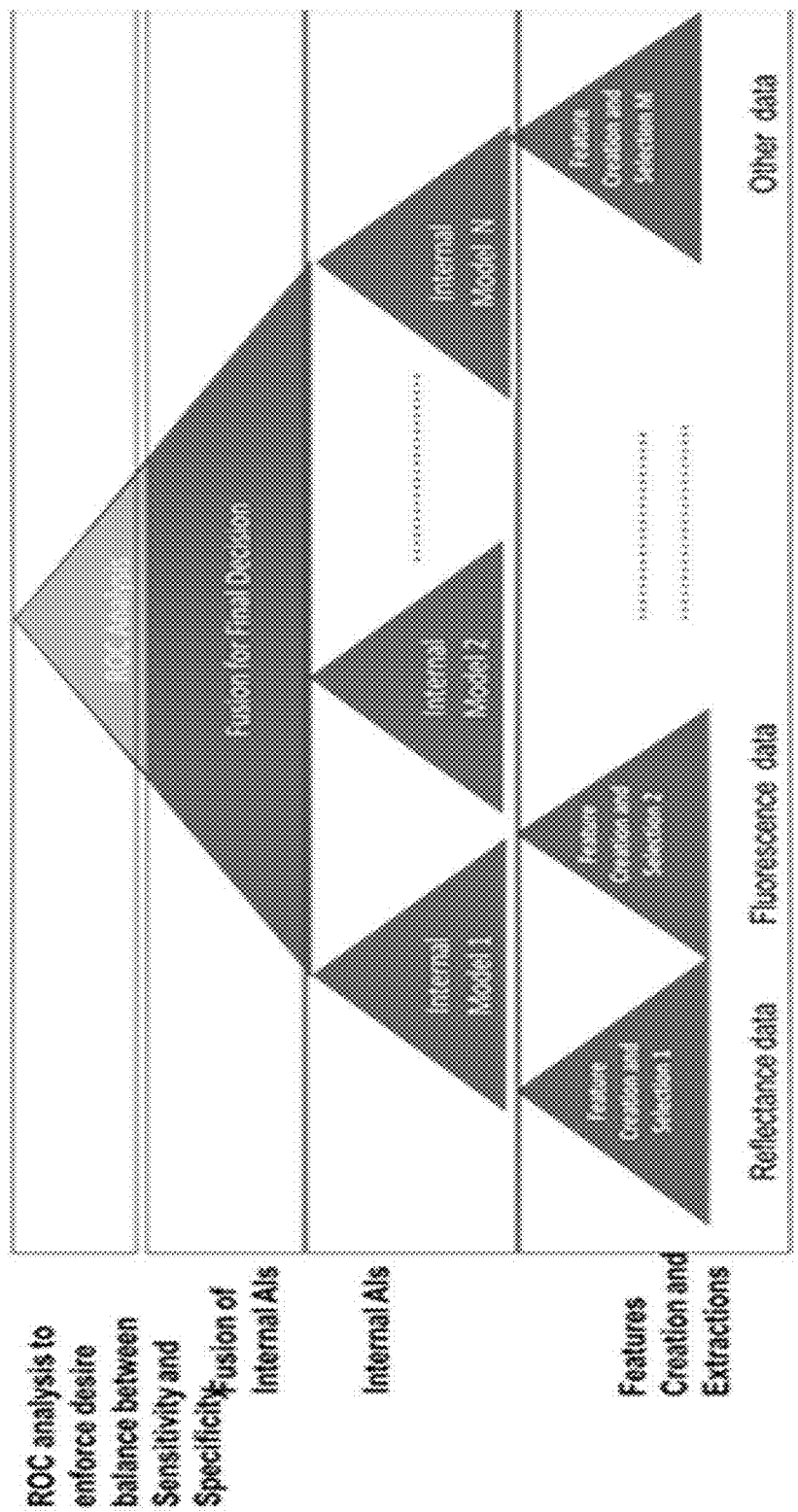
FIG. 6 is a conceptual representation of artificial intelligence employable or employed in and/or with the current design.

FIG. 6 illustrates the proposed architecture and high-level steps. Level 1 includes Signal Conditioning, Feature extraction and Feature selection. Level 2 includes all trained models for different applications and classes. Level 3 fuses internal decisions (AI scores) coming from all internal AI models to get a final AI score. Level 4 applies a receiver operating characteristic (ROC), representing the diagnostic ability of the Classifiers as the discrimination threshold is varied, to enforce desired balance between specificity and sensitivity of the AI system.

Processing of this type may be divided into two modules, feature extraction and classification. The feature extraction module processes the raw data into a low dimensional feature vector that is relatively invariant to distortions and artifacts and is high in information content, making it suitable to be used by the Classifier stage. Prior knowledge about the data and the experience acquired on building similar systems may be employed. This stage of machine learning (ML) may require experimentation and fine-tuning by hand. The Classifier is usually chosen from the large number of available generic modules and is trained using available data.

The present system may employ a numerical computing framework, such as MATLAB, for model development and validation. The observations (input data) are raw measurements obtained by the system. Training set class "labels" may be provided by DNA analysis. In the fish example, data may be collected from at least 15 types of fish and used for the classification pipeline model selection and validation, and secondarily used as a holdout set of some number, such as 100, fish for classifier final testing. In the first stage, internal Classifiers are trained separately. A final classifier is obtained by fusing the prediction of several internal classifiers (models).

Figure 7:
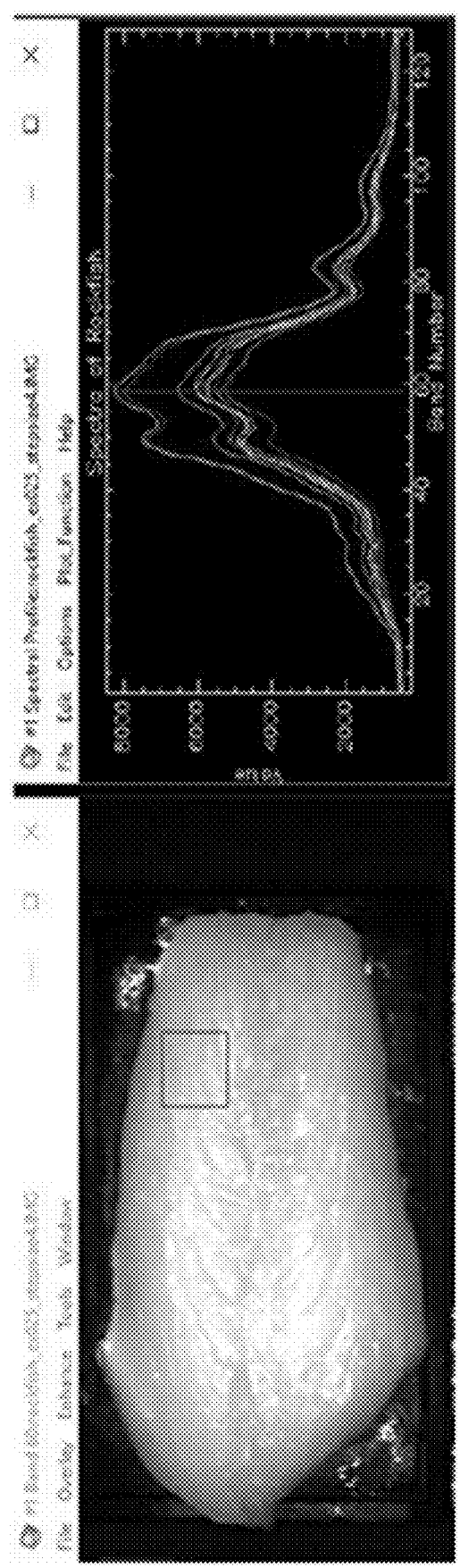
FIG. 7 illustrates biological samples, specifically fish, and reflectance spectral signatures of the biological samples.
Figure 8:
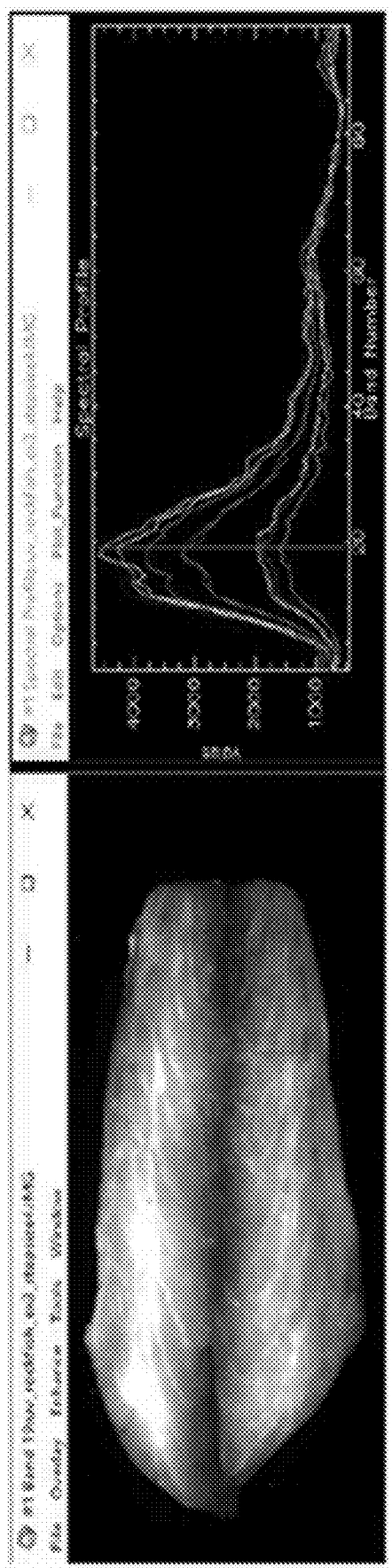
FIG. 8 illustrates biological samples (fish), and florescence spectral signatures of the biological samples

Thus the system employs spectral acquisitions (raw signals) where raw data includes fluorescence and reflectance spectral data and correlative fish DNA results. FIG. 7 illustrates reflectance results while FIG. 8 shows florescence results, representing typical raw data signals. Fish fillets are imaged on the left, with acquired spectral signatures shown ion the right. Data may be collected from any number of cases and used for classification pipeline model selection and validation. A holdout set may be employed for Classifier final testing.

The system performs signal conditioning to reduce data variability caused by differences in hardware probes and operating conditions. This includes probe-specific calibration, dark current removal, and wavelength alignment to a unique set of wavelengths via interpolation. In addition, the system uses signal-to-noise, signal validation and saturation tests to reject bad data samples.

Data may be initially calibrated prior to feeding to the classification pipeline, based on individual spectroscopic data acquisition system characteristics. The extraneous parts of the signal may be truncated from the reflectance and fluorescence signals. Valid wavelength ranges may be obtained by examining raw data, automatically or manually, or performing an optimization and exhaustive search to find valid wavelength ranges.

The system may perform wavelength alignment using interpolation. Because the spectrometer cannot be calibrated such that the response is measured exactly at the same wavelengths for all units, the system may employ a reference wavelength grid to compare collected signals. The system may obtain the signal aligned to the reference grid from the raw signal using a cubic or linear spline interpolation from values measured by a spectrometer, and these values may be used by the pipeline.

After initial signal conditioning, the system may extract features from the raw data. Processing of conditioned data into a low dimensional feature vector creates features that are relatively invariant to distortions and artifacts and valuable informational content. This combination makes the results of this stage suitable to be used in the Classifier stage.

The system, or those providing functionality for the system, may use prior knowledge about the data during this stage to determine optimal methods of feature extraction. These include original raw data in linear or log space, wavelet transform, statistical features, and textural features. The system may use feature level fusion by combining into a single vector feature vector. The system may determine or provide a separate AI model for each feature type and will fuse outcomes of each AI in decision levels as well.

The system may perform feature selection using methods such as Principal components analysis (PCA) and Independent Component Analysis (ICA) algorithms for dimensionality reduction and removing redundant features and information.

PCA is a statistical method that converts a set of observations and sensor data with some level of redundancy and correlation into a set of uncorrelated components called principal components by use of an orthogonal transformation.

Independent component analysis (ICA) decomposes a multivariate signal into statistical independent non-Gaussian components. ICA could be used for feature selection and reduction. We stack our raw data vectors in a matrix where each row is an observation. ICA reduces the number of columns or rearranges the information in the raw data into a smaller number of features.

The system normalizes features using methods including but not limited to z-score area under the curve (AUC).

For low level (internal) algorithms, a number of models may be employed: Deep learning techniques including conventional neural network (CNN) and tensor flow, Artificial Neural Networks; Support Vector Machines (SVM) including linear, non-linear; AdaBoost.

All of these machine learning methods are supervised binary classification models. A binary classifier is a numerical pipeline which has as input a numerical vector and outputs a binary decision, assigning the input membership to one of two classes.

A deep learning model continually analyzes data with a logic structure similar to how a human would draw conclusions. To achieve this, deep learning uses a layered structure of algorithms called an artificial neural network (ANN). The design of an ANN is inspired by the biological neural network of the human brain. This makes for machine intelligence that's far more capable than that of standard machine learning models.

Differences between classical machine learning and AI versus deep learning include: machine learning uses algorithms to parse data, learn from that data, and make informed decisions based on what has been learned; deep learning structures algorithms in layers to create an "artificial neural network" that can learn and make intelligent decisions on its own; and deep learning is a subfield of machine learning. While both fall under the broad category of artificial intelligence, deep learning powers the most human-like artificial intelligence.

Figure 9:
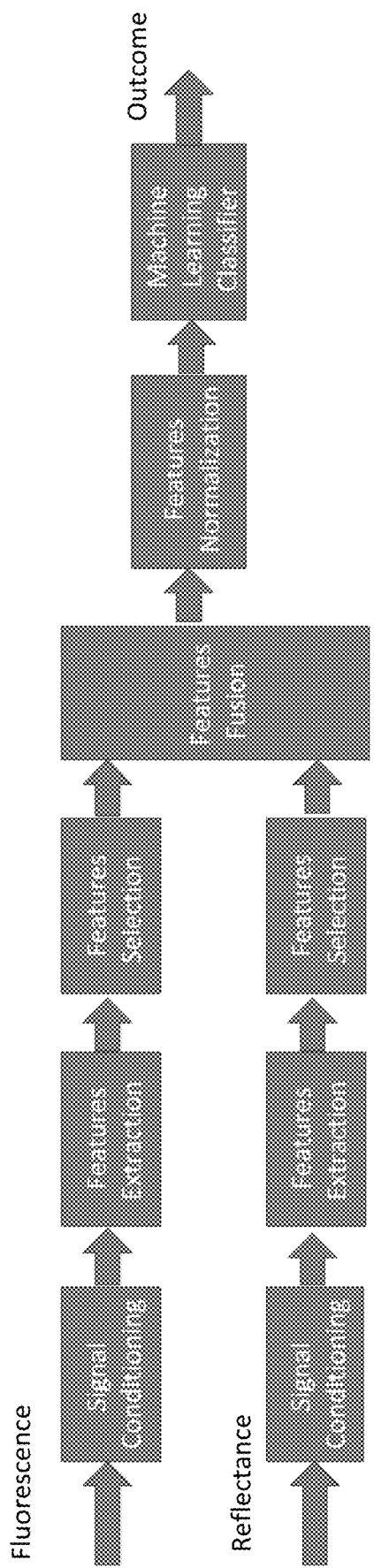
FIG. 9 is an example embodiment of an internal artificial intelligence model.

The system may partition the data, with approximately 70% used for training and 30% for testing. The process may be repeated multiple times to test if data is independent and identically distributed and is exchangeable. Such processing can help to evaluate intAI (internal AI) performance by calculating mean and confidence interval for intAI performance. FIG. 9 shows one intAI architecture with feature extraction and selection (Extraction) prior to executing intAI.

The top level in the AI architecture of FIG. 9 is "fusion." At this level, the system fuses internal (low-level) algorithms results (decisions) to obtain a final decision. With selected Classifiers, the system computes a weighted sum of Classifier decisions/score. The system makes a global decision by comparing this sum to a threshold.

From FIG. 9, there is provided a fluorescence path and a reflectance path, where fluorescence passes fluorescence image readings to an input data conditioning element, which in turn passes data to feature extraction and selection modules. Reflectance passes reflectance image readings to signal conditioning modules to align data using interpolation grid and filter invalid data using data quality filters such as SNR (signal-to-noise ratio). If features level fusion of fluorescence and reflectance data is desired, a similar data processing chain could be applied to reflectance data as well. The features coming from fluorescence and reflectance data are fused. After normalization the fused features are fed to a machine learning model. An alternate representation of the processing is presented in FIG. 11.

With respect to AI training and internal Models Selection Process, the system may perform an exhaustive search and optimization to find best internal and fusion models. For the pipeline, the system starts with a machine learning model such as is outlined above. The system may then optimize the parameters of the model, seeking to maximize performance. With respect to an intAI model selection, the system may perform selection of the best classification pipeline model using an exhaustive search process over the possible combinations of algorithms and control parameters for each stage. At each point in the exhaustive search evaluation, the system may apply a data partitioning to use a portion of data for optimization and the remaining for cross-validation test. The main performance selection criterion is the average sensitivity/specificity for all the cross-validation tests. The system may perform deeper analysis on Classifiers, which may be individual software or hardware components or modules or combinations thereof, that have passed a performance threshold (e.g., find an operating point on the ROC with at least 95% sensitivity and maximum specificity among other Classifiers).

The final model is fine-tuned using the training set for best performance. After data partitioning, a portion of data for AI training and the remaining for validation of trained AI models. The parameters of each stage may be fine-tuned around the values selected in the previous step. The system may run this process multiple times to select the model with the best performance. The architecture of the models is the same but the control parameters for each stage are datadriven and determined by partitioning of the training data set. The system may validate the final model using the hold-out data set.

The design may include a wireless, portable high-speed device for assessment of food samples which is deployable to current field measurement demands. One such system may employ, for example three modes of spectral measurement:

Visible-NIR spectroscopy that surpasses human vision capability (with spectral resolution at nm level) and facilitate compositional analysis Fluorescence spectroscopy, focusing on molecular structure as well as protein, and harmful biomaterial detection and analysis (e.g. toxins, spoilage, harmful bacteria)

IR spectroscopy to characterize chemometric aspects of our specimens, such as water, protein, fat and carbohydrate characteristics using classical absorption spectroscopy.

The present system employs multimode settings to cross-validate each mode of measurement. For instance, the system can acquire pure fluorescence measurements independent of light absorption (color) by reflectance and fluorescence in concurrent measurements. By analyzing food samples, for example, using multimode methods, the system can more accurately differentiate the target of interest, and can analyze substantially more information, thus addressing a wider range of characteristics and drawing deeper and more discrete conclusions (i.e. more targeted and valuable signatures). The AI algorithm may train itself over time to be more efficient, where more efficient means higher accuracy and faster assessment.

One example of multimode spectral measurement involves the measurement of pure fluorescence spectra independent of light absorption. Natural fluorescence in food samples can be excited in multiple wavelength ranges. Examples include 278 nm (targeting Vitamin B2, tyrosine, and tryptophan), 305 nm (Targeting Vitamin B6, Vitamin E, and ATP), 365 nm (NADH, Vitamin A), 395 nm (hematoporphyrin), and 405 nm (chlorophyll). However, individual food sample may absorb light differently at excitation or emission wavelengths. By independently characterizing reflectance spectra, the system can minimize the absorption contribution to the fluorescence spectra and purify fluorescence spectral signatures.

A second example of multimode operation (multi excitation fluorescence) is to more effectively unmix the fluorophores contributions of the food sample. Usually, emission spectra of natural fluorophores are broad and overlap to other natural fluorophores. Multiple excitation wavelengths helps to differentiate individual fluorophores. Some of the molecules have specific absorption characteristics that can be individually calculated and to be used to improve fluorescence unmixing progress. Thus according to the present design, multimode may include using a single technique in varying ways, such as at different frequencies or wavelengths.

Machine Learning operation of the present system can identify which spectral features are important to differentiate between biological samples such as food samples. Such machine learning helps the Classifier to weight specific molecular, compositional components relative to each other for final classification. Machine learning also trains the expert system which combination of compositional, molecular, or chemical components becomes relevant and potentially important for classification optimization. Artificial intelligence in the system can establish a strategy where the classification can be optimized for either speed and/or accuracy by filtering most differentiating spectral features and removing the redundant data.

Figure 10:
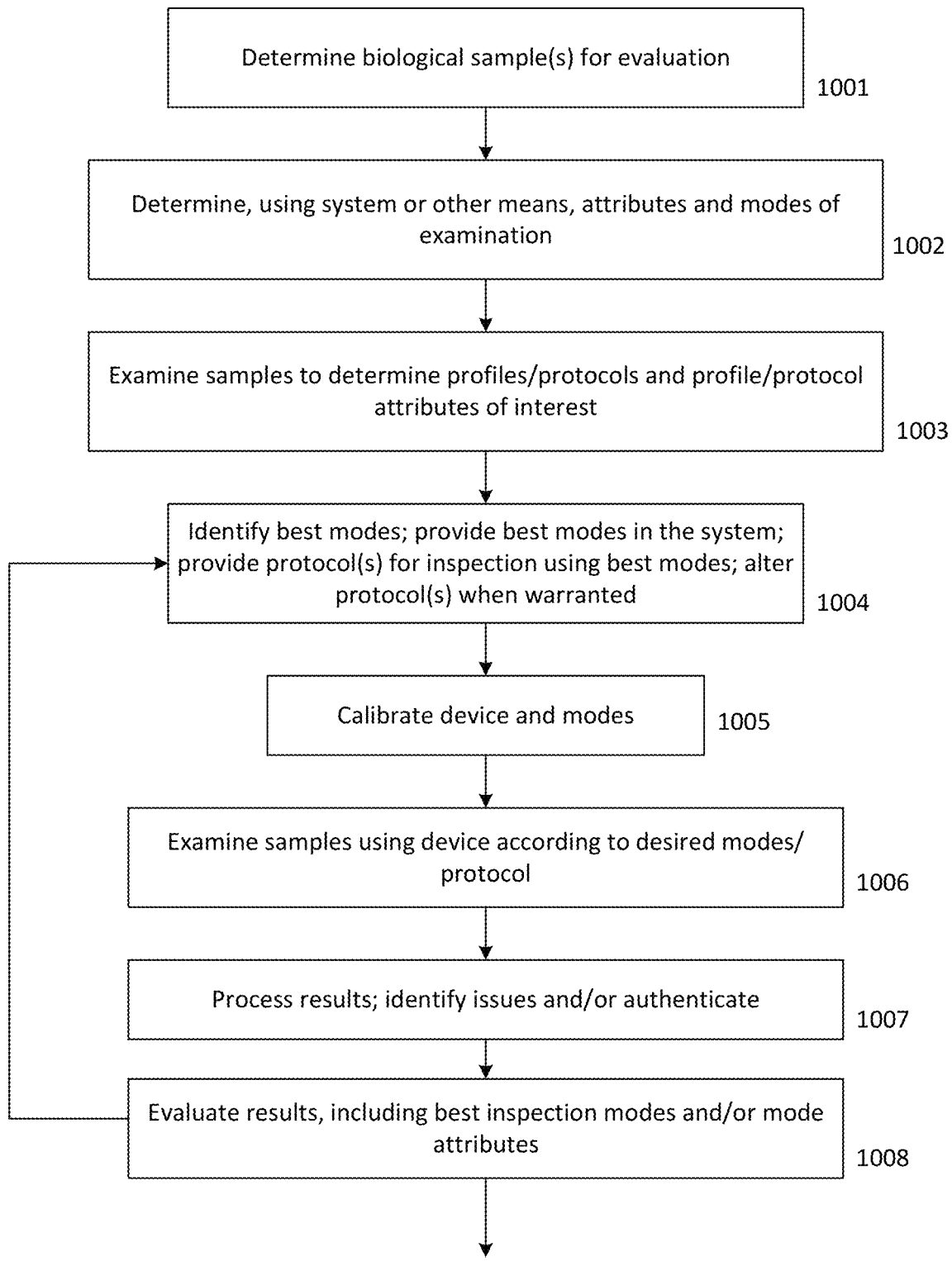
FIG. 10 is a conceptual overview of operation according to the present design.

A general overview of the present design is thus presented in FIG. 10. At point 1001, the system determines the biological sample(s) for evaluation. For example, the system may be desired to process only fish, or may process beef and pork, or may process fruits, vegetables, and occasional meats of various kinds. This may be established by users or automatically, such as by a user being offered options and selecting those applicable. At point 1002, the system determines, using the components offered and/or other means, attributes of samples for examination and modes of examination. For example, a sample may call for examination using Raman spectroscopy and infrared scanning, either by experience or based on previous observations. In some instances, the samples be examined may have no known best mode used, and thus experimentation may be required to determine the desired use of mode X on sample Y. Point 1003 is optional, wherein the system examines samples to determine sample profiles and profile attributes of interest. For example, a sample with a particular known contaminant may be examined using speckle imaging and it may be determined that when examining at a particular wavelength, the presence of the contaminant becomes particularly pronounced, and thus all samples may be examined using speckle imaging at the particular wavelength to determine the presence of the contaminant. Alternately, if a biological sample such as a plant from a particular location exhibits an attribute under infrared imaging, similar plant samples may be examined using similar infrared imaging.

Point 1004 calls for identifying best modes and ensuring the best modes are available in the design. The various modes shown in FIG. 4 may be employed, but other modes may be provided as suggested. In some instances, examination in a single mode at various frequencies, wavelengths, or other measurement quantities may be employed. Such modes and examination attributes may be offered according to an examination and analysis protocol. If it is determined that samples of interest must be examined at wavelength P in mode Q, mode Q must be offered and must be able to operate at wavelength P. Point 1005 represents generally the initiation of production, i.e. the examination of multiple samples according to the present design, wherein the device and modes are calibrated. Point 1006 calls for examining samples using the device in the desired modes using the desired attributes, or in other words, according to the examination and analysis protocol.

At point 1007, the system processes results, including making assessments as to presence or absence of attributes, authentication probabilities, and so forth. Such processing employs the artificial intelligence and machine learning described herein. At point 1008, the system may evaluate and assess results, again using known attributes, machine learning, artificial intelligence, and/or other techniques. Results from this step importantly are fed back to point 1004, conceptually representing decisions to alter the examination and analysis protocol as well as the mode or modes employed. As an example, the system may process thousands of samples of beef using a given protocol, such as examining using reflectance multiwavelength imaging at three different wavelengths. However, examination at these wavelengths may offer limited results, such as a failure to determine the cut of beef being examined. In other words, results provided may be inconclusive. As a result, the system may augment the protocol and examination by adding a different mode or may add a wavelength to the three wavelengths used for examination. Thus the present system employs feedback of determined results to improve the overall protocol and the overall examination and analysis process, and the protocol established may be dynamically changed depending on circumstances encountered.

Figure 11:
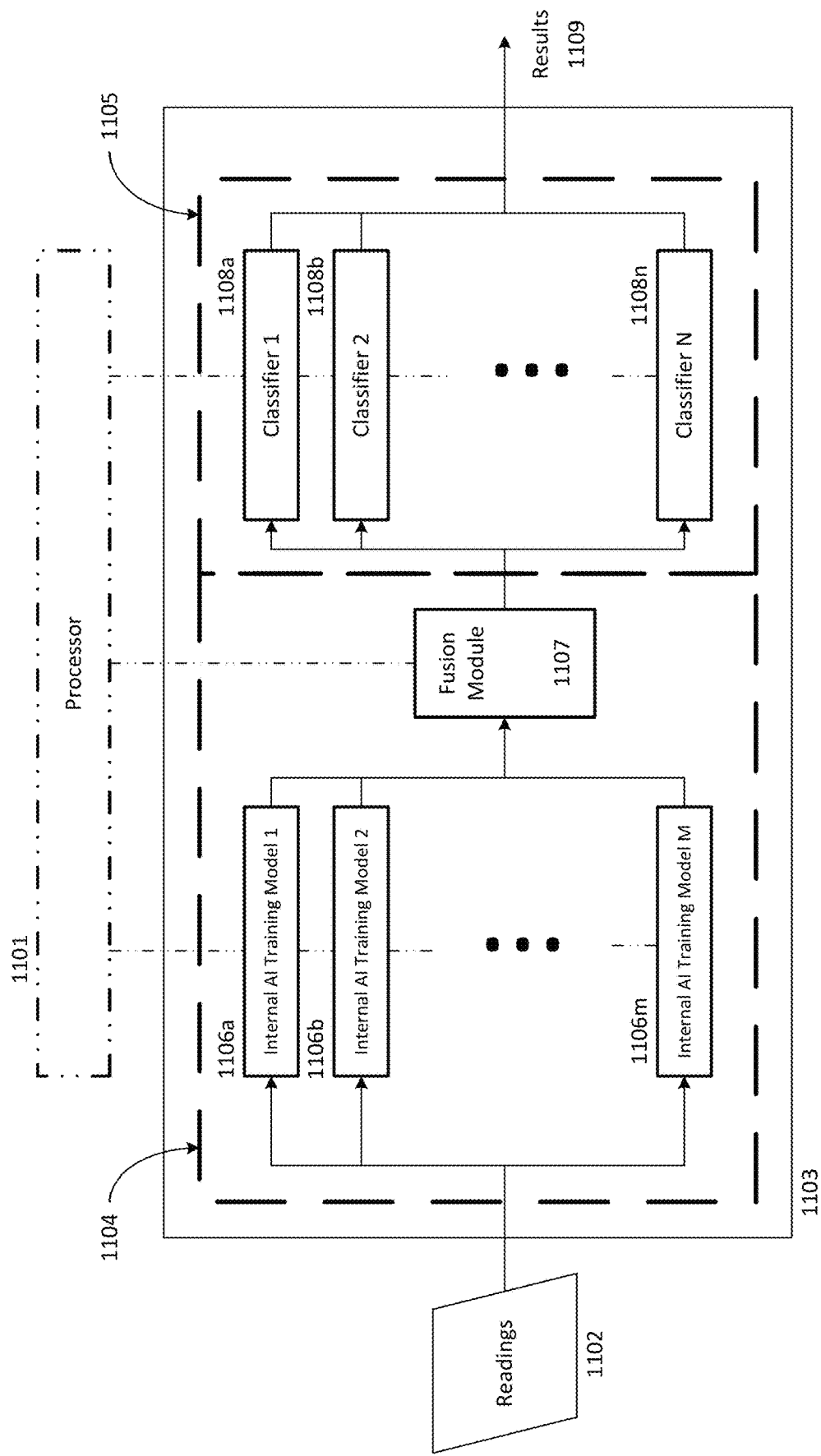
FIG. 11 shows an alternate embodiment of the processing according to the present design.

FIG. 11 is a general overview of the processing modules employed. More or different modules may be employed. From FIG. 11, processor 1101 controls all processing, including applicable machine learning, artificial intelligence, and the like. Point 1102 represents readings taken, which are received by the processing arrangement 1103. Processing arrangement 1103 includes feature extraction module 1104 and classifier module 1105. The readings are received and distributed to the various internal AI training models 1106a through 1106m which generally identify known aspects and attributes from the readings based on experience and/or prior readings. A single internal AI training model may be employed or offered. Fusion module 1107 fuses the results from the various internal AI training models 1106a through 1106m. Classifiers 1108a through 1108n classify the fused results as described above, and overall results are provided at point 1109. Processor 1101 may then operate to provide the feedback shown in FIG. 10, determining that different modes and/or different assessments may be employed or different attributes examined, for example.

Thus according to one embodiment, there is provided a biological sample inspection apparatus, comprising an illumination hardware arrangement comprising transmission and sensing hardware, the illumination hardware arrangement configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes, wherein the processing hardware receives scan results from the illumination hardware arrangement and identifies attributes of the biological sample. The processing hardware is configured to employ the attributes of at least one biological sample to alter the protocol.

According to a further embodiment of the present design, there is provided a method for inspecting at least one biological sample, comprising determining a plurality of inspection modes for inspecting the at least one biological sample using a multimode inspection apparatus, determining an inspection protocol for inspecting the at least one biological sample, wherein the inspection protocol comprises inspection settings for the plurality of inspection modes, inspecting the at least one biological sample using the multimode inspection apparatus according to the protocol, and altering the protocol based on inspection results for multiple biological samples.

According to another embodiment of the present design, there is provided a biological sample inspection apparatus configured to inspect a biological sample for issues, comprising illumination hardware comprising transmission and sensing hardware configured to illuminate and sense attributes of the biological sample, the illumination hardware configured to inspect the biological sample using multiple inspection configurations from at least one of a fluorescence imaging mode, a reflectance imaging mode, a scattering imaging mode, and a Raman imaging mode, and processing hardware configured to operate the illumination hardware according to a protocol comprising inspection settings for the multiple inspection configurations, wherein the processing hardware receives scan results from the illumination hardware and identifies attributes of the biological sample. The processing hardware is configured to employ the attributes of at least one biological sample and alter the protocol based on the attributes of the one biological sample.

According to a further embodiment of the present design, there is provided a biological sample inspection apparatus, comprising an illumination hardware arrangement comprising transmission and sensing hardware configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample by constructing a multidimensional dataset comprising at least one spatial dimension and at least one spectral dimension from the scan results and analyzing the multidimensional dataset. The processing hardware is configured to employ the attributes of at least one biological sample and alter the protocol.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another, i.e. may include transitory and/or non-transitory computer readable media. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A biological sample inspection apparatus, comprising:
an illumination hardware arrangement comprising transmission and sensing hardware configured to inspect a biological sample using at least two modes from a group comprising:
  a fluorescence imaging mode;
  a reflectance imaging mode;
  a scattering imaging mode; and
  a Raman imaging mode; and
processing hardware configured to operate the illumination hardware arrangement according to a protocol comprising inspection settings of the at least two modes;
wherein the processing hardware receives scan results from the illumination hardware arrangement and identifies attributes of the biological sample by constructing a multidimensional dataset comprising at least one spatial dimension and at least one spectral dimension from the scan results and analyzing the multidimensional dataset;
wherein the processing hardware is configured to employ the attributes of at least one biological sample and alter the protocol.

* * * * *